United States Patent
Nagel et al.

(10) Patent No.: US 9,180,246 B2
(45) Date of Patent: Nov. 10, 2015

(54) MEDICAMENT CONTAINER

(75) Inventors: Thomas Nagel, Tharandt (DE); René Richter, Tharandt (DE); Robert Witt, Dresden (DE)

(73) Assignee: SANOFI-AVENTIS DEUTSCHLAND GMBH, Frankfurt Am Main (DE)

( * ) Notice: Subject to any disclaimer, the term of this patent is extended or adjusted under 35 U.S.C. 154(b) by 724 days.

(21) Appl. No.: 13/391,736

(22) PCT Filed: Sep. 8, 2010

(86) PCT No.: PCT/EP2010/063137
§ 371 (c)(1),
(2), (4) Date: Aug. 10, 2012

(87) PCT Pub. No.: WO2011/029828
PCT Pub. Date: Mar. 17, 2011

(65) Prior Publication Data
US 2012/0291778 A1    Nov. 22, 2012

(30) Foreign Application Priority Data
Sep. 10, 2009    (EP) .................................... 09169895

(51) Int. Cl.
A61M 11/00    (2006.01)
A61M 5/148    (2006.01)
A61M 11/06    (2006.01)

(52) U.S. Cl.
CPC ............. A61M 5/148 (2013.01); A61M 11/008 (2014.02); A61M 11/06 (2013.01); *A61M 2205/0266* (2013.01); *A61M 2205/0288* (2013.01); *A61M 2205/3368* (2013.01)

(58) Field of Classification Search
CPC ....... A61M 5/172; A61M 5/20; A61M 5/148; A61M 11/06; A61M 2205/0266; A61M 2205/0288; A61M 2205/3368; A61M 11/08; A61J 1/10; A61J 2001/201; A61J 1/14
USPC ............. 128/200.22, 200.14, 200.23, 200.24, 128/203.12; 222/94, 107, 386.5; 220/62.22, 220/62.21, 62.29, 62.11, 9.1, 9.2; 206/521; 141/114
See application file for complete search history.

(56) References Cited

U.S. PATENT DOCUMENTS 4,088,166 A * 5/1978 Miller ........................... 604/408
4,136,802 A * 1/1979 Mascia et al. .................... 222/95

(Continued)

FOREIGN PATENT DOCUMENTS

| DE | 10219750 | 7/2003 |
| WO | 02/058765 | 8/2002 |
| WO | 2009/069518 | 6/2009 |

OTHER PUBLICATIONS

International Preliminary Report on Patentability for International App. No. PCT/EP2010/063137, issued Mar. 13, 2012.

(Continued)

*Primary Examiner* — Steven Douglas
(74) *Attorney, Agent, or Firm* — McDonnell Boehnen Hulbert & Berghoff LLP

(57) ABSTRACT

The apparatus relates to a medicament container for a liquid medicament. The medicament container comprises a deformable bag with an outlet and at least one deformation member consisting of a shape memory alloy. The at least one deformation member is arranged to deform the deformable bag when the shape memory alloy passes from a first phase into a second phase by a phase transition, thereby changing the shape of the deformation member and squeezing a dose of the medicament through the outlet out of the bag.

10 Claims, 1 Drawing Sheet

(56) References Cited

U.S. PATENT DOCUMENTS 5,685,456 A * 11/1997 Goldstein .................. 222/95
6,096,007 A * 8/2000 Haan et al. ................ 604/147
7,175,894 B2 * 2/2007 Nakamura ................. 428/35.2

OTHER PUBLICATIONS

International Search Report for International App. No. PCT/EP2010/063137, completed Feb. 2, 2011.

* cited by examiner

MEDICAMENT CONTAINER

CROSS REFERENCE TO RELATED APPLICATIONS

The present application is a U.S. National Phase Application pursuant to 35 U.S.C. §371 of International Application No. PCT/EP2010/063137 filed Sep. 8, 2010, which claims priority to European Patent Application No. 09169895.1 filed on Sep. 10, 2009. The entire disclosure contents of these applications are herewith incorporated by reference into the present application.

FIELD OF INVENTION

The invention relates to a medicament container for a liquid medicament, the medicament container comprising a bag with an outlet.

BACKGROUND

Many medicaments have to be injected into the body. This applies in particular to medicaments, which are deactivated or have their efficiency remarkably decreased by oral administration, e.g., protein (such as insulin, growth hormones and interferons), carbohydrates (e.g. heparin), antibodies and the majority of vaccines. Such medicaments are predominantly injected by means of syringes, medicament pens or medicament pumps.

Some medicaments have to be administered by inhaling them from so called inhalers.

WO 2009/069518 A1 discloses an inhaler, wherein the medicament to be inhaled is stored in a bag shaped medicament container.

WO 02/058765 A1 discloses a drug delivery device which can be implanted in a patient. The drug delivery device includes a reservoir for the drug with at least one discharge outlet through which the drug can be discharged. A drive member comprising a shape memory alloy is arranged in the device in a deformed configuration to act against the reservoir directly or indirectly by recovering from its deformed configuration by virtue of its elastic properties to cause the volume of the reservoir available for the drug to be reduced and to cause drug in the reservoir to be discharged from the reservoir.

DE 102 19 750 C1 discloses a medicament container for a liquid medicament, the medicament container comprising a deformable bag with an outlet and at least one deformation member consisting of a shape memory alloy and arranged to deform the deformable bag when the shape memory alloy passes from a first phase into a second phase by a phase transition, thereby changing the shape of the deformation member and squeezing a dose of the medicament through the outlet out of the bag.

SUMMARY

It is an object of the present invention to provide an improved medicament container providing a better control of delivery.

The object is achieved by a medicament container according to claim 1.

Preferred embodiments of the invention are given in the dependent claims. A medicament container for a liquid medicament according to the invention comprises a deformable bag with an outlet and at least one deformation member consisting of a shape memory alloy. The at least one deformation member is arranged to deform the deformable bag when the shape memory alloy passes from a first phase into a second phase by a phase transition, thereby changing the shape of the deformation member and squeezing a dose of the medicament through the outlet out of the bag.

The medicament container comprises several consecutive deformation members. Several independently actuatable deformation members provide a better control of delivery by emptying the bag incrementally by activating the deformation members one after the other. This is advantageous, for instance, when a medicament is to be administered in several consecutive doses.

By means of a deformation member consisting of a shape memory alloy, the deformable bag can be deformed in a definite manner when the shape memory alloy passes from a first phase into a second phase. Arranging the deformation member appropriately, the deformation of the bag squeezes a dose of the medicament through the outlet out of the bag. The inventive design thereby allows pressing the medicament out without external displacing mechanisms like piston rods. Friction is avoided since no movable parts are required. Furthermore the invention allows for very lightweight, compact and cheap medicament containers.

In a preferred embodiment of the invention the medicament container comprises temperature regulation means for changing the temperature of a deformation member to cause the phase transition of its shape memory alloy. This allows to cause a change of the shape of a deformation member and a discharge of medicament by changing the temperature of a deformation member.

The temperature regulation means may comprise electrical connections for each deformation member to connect it to an electrical power supply. This allows controlling the temperature of the deformation members in a simple and effective manner by means of electrical power.

In an alternative embodiment the shape memory alloy is a magnetic shape memory alloy. Phase transitions of such alloys changing them in shape or size can be induced by applied magnetic fields. The use of such alloys has the advantage that a phase transition caused by a magnetic field can be faster and more efficient than a temperature induced phase transition.

Accordingly, in this embodiment the medicament container comprises preferably at least one magnetic field generator to generate a magnetic field to cause the phase transition of the magnetic shape memory alloy.

Preferably at least one deformation member stretches out over at least part of a longitudinal extension of the bag. This allows deforming at least part of the bag by means of a deformation member.

Preferably at least one deformation member is located at an outer surface of the bag. Such a location allows compressing the bag by constricting at least part of the bag by a deformation member located at its outer surface.

In one embodiment at least one deformation member stretches out straightly in the first phase of its shape memory alloy and is rolled up spirally in the second phase of its shape memory alloy. Rolling up a deformation member in this manner, the deformable bag can be rolled up such that medicament is discharged through the outlet of the bag.

Preferably this embodiment of the medicament container comprises a core around which the at least one deformation member is rolled up spirally in the second phase of its shape memory alloy. The core defines an axis around which the deformation member is rolled up and thereby controls and stabilizes advantageously the manner in which the deformation member is rolled up. Furthermore the core avoids that a substantial amount of medicament remains inside the bag when the deformation member is rolled up, thereby improving the accuracy of the administration of a dose of the medicament and reducing the leftovers inside the bag after administration which is advantageous especially in the case of expensive medicaments.

Alternatively or additionally at least one deformation member stretches out as a helix around the bag, the radius of the helix being smaller in the second phase than in the first phase of the shape memory alloy. In this embodiment the bag is wrapped with a helix shaped deformation member and can be constricted and compressed by reducing the radius of the helix when the shape memory alloy passes from the first phase to the second phase, thereby discharging medicament through the outlet of the bag.

Preferably this embodiment of the medicament container comprises a core stretching out over the axis of the helix. The core defines an axis around which the deformation member spirals and thereby controls and stabilizes advantageously the shrinking of the helix when the shape memory alloy passes from the first phase to the second phase. Furthermore the core avoids that a substantial amount of medicament remains inside the bag which provides the above mentioned advantages.

In a further embodiment the medicament container comprises several consecutive deformation members and preferably temperature regulation means or at least one magnetic field generator to cause phase transitions of the shape memory alloy of the deformation members independently of one another. Such an embodiment allows emptying the bag incrementally by activating the deformation members one after the other. This is advantageous, for instance, when a medicament is to be administered in several consecutive doses.

The outlet may comprise an interface for receiving a hollow injection needle. Alternatively, the needle may be integrated with the medicament container.

The medicament container may be part of an injection arrangement or an inhaler arrangement for delivering a liquid medicament to a human or an animal.

The injection arrangement may comprise a valve and a hollow needle for piercing a patient's skin, the valve and needle being arranged at the outlet of the medicament container. In case of a jet injector, instead of the needle, a jet nozzle may be arranged.

The medicament container may be used for delivering one of an analgesic, an anticoagulant, insulin, insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
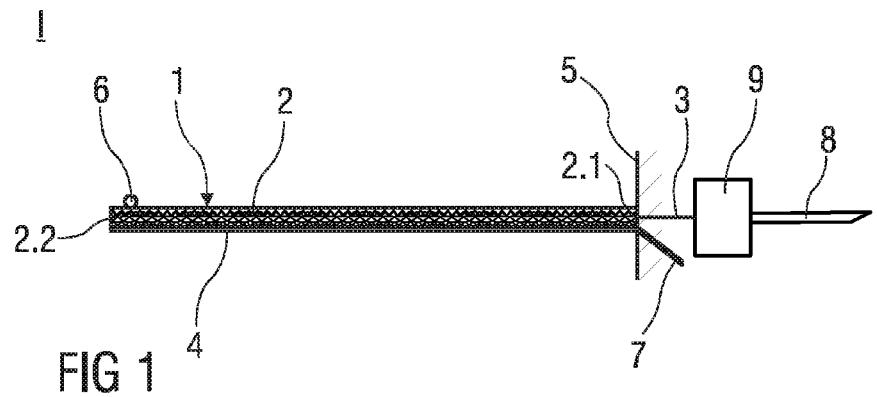
FIG. 1 is a schematic lateral view of a medicament container comprising a deformable bag and a deformation member consisting of a shape memory alloy and stretching out straightly along a longitudinal axis of the bag in a first phase of the shape memory alloy.

FIG. 1 shows a schematic lateral view of a first embodiment of a medicament container 1 which is part of an injection arrangement I for delivering a liquid medicament. The medicament container 1 comprises an elongate deformable bag 2 with an outlet 3 and a deformation member 4.

The deformation member 4 consists of a shape memory alloy and stretches out straightly along a longitudinal axis of the bag 2 in a first phase of the shape memory alloy. The deformation member 4 is located at an outer surface of the bag 2 and firmly attached to it.

The bag 2 stores a liquid medicament. The outlet 3 is located at a first end 2.1 of the bag 2 which is fixed to a housing 5 for the medicament container 1. Close to a second end 2.2 of the bag 2, the medicament container 1 comprises a rigid core 6 which is located at the outer surface of the outlet 3 at a side opposite to the side where the deformation member 4 is located and is firmly attached to the bag 2.

The deformation member 4 is connected via electrical connections 7 to an electrical power supply through which electrical energy can be supplied to the deformation member 4 to cause a phase transition of the shape memory alloy.

The injection arrangement I further comprises a hollow needle 8 for piercing a patient's skin. The needle 8 is connected to the outlet 3 so that the medicament can flow from the interior of the bag 2 through the outlet 3 to the needle 8. The injection arrangement I shown in FIG. 1 further comprises an interface 9 for attaching the needle 8 to the outlet 3. The interface 9 may comprise a thread which has a mating thread in the housing 5. In an alternative embodiment the needle 8 may be firmly attached to the housing 5 or the medicament container 1 without an interface 9.

Figure 2:
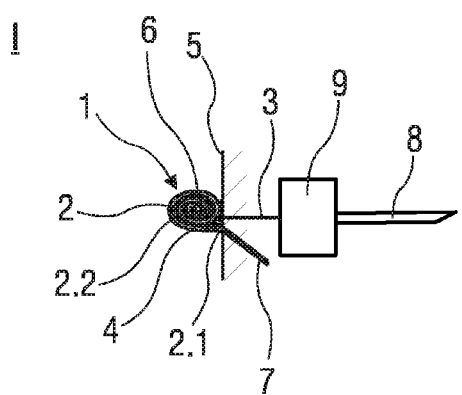
FIG. 2 is a schematic lateral view of the medicament container of FIG. 1 in a second phase of the shape memory alloy in which the deformation member and the bag are rolled up spirally.

FIG. 2 shows a schematic lateral view of the medicament container 1 in the injection arrangement I of FIG. 1 in a second phase of the shape memory alloy. In the phase the deformation member 4 is rolled up spirally from a second end meeting the second end 2.2 of the bag 2 to a first end meeting the first end 2.1 of the bag 2. Owing to the presence of the core 6 attached to the second end 2.2 of the bag 2 and the attachment of the deformation member 4 to the outer surface of the bag 2, the deformation member 4 spirals around the core 6 and thereby rolls up and compresses the bag 2 such that the medicament is squeezed out of the bag 2 through the outlet 3 towards the needle 8. The fixing of the first end 2.1 of the bag 2 to the housing 5 thereby serves to maintain the connection of the interior of the bag 2 to the outlet 3.

The phase transition of the shape memory alloy from its first phase to its second phase is caused by supplying an amount of electrical energy to the deformation member 4 through the electrical connections 7 to sufficiently increase the temperature of the shape memory.

Figure 3:
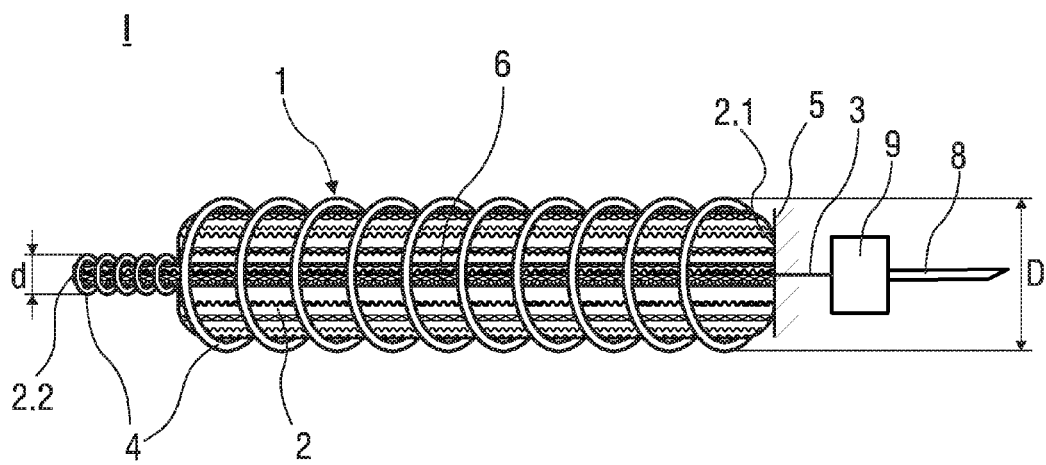
FIG. 3 is a schematic lateral view of a medicament container comprising a deformable bag and several consecutive loops like deformation members consisting of a shape memory alloy, each deformation member winding once around the bag with a diameter depending on the phase of respective shape memory alloy.

FIG. 3 shows a schematic lateral view of a second embodiment of a medicament container 1 in an injection arrangement I. As in the first embodiment shown in FIGS. 1 and 2, the medicament container 1 comprises an elongate deformable bag 2 to store a liquid medicament, and a first end 2.1 of the bag 2 is fixed to a housing 5 of the bag 2 at an outlet 3 of the bag 2 connected to a needle 8.

In contrast to the first embodiment, the medicament container 1 comprises several consecutive loop like deformation members 4 consisting of a shape memory alloy. Each deformation member 4 winds once around the bag 2 in a plane approximately orthogonal to a longitudinal axis of the bag 2.

Furthermore the medicament container 1 comprises a core 6 which extends out straightly and approximately parallel to this longitudinal axis from the first end 2.1 to a second end 2.2 of the bag 2. The core 6 may be located in the interior of the bag 2 or at an outer or inner surface of the bag 2. If it is located in the interior of the bag 2, it is arranged such that it does not lock up the outlet 3. If it is located at the outer surface of the bag 2, it is fed through all the loop like deformation members 4 so that each deformation member 4 winds around the core 6.

In the first phase of the shape memory alloy, a deformation member 4 has a first diameter D. In a second phase it is a second diameter d which is smaller than the first diameter D. Hence, when passing from the first phase to the second phase, a deformation member 4 shrinks in size and thereby compresses the bag 2 at the location where it winds around the bag 2.

The medicament container 1 comprises temperature regulation means (not shown) to change the temperature of the consecutive deformation members 4 independently of one another. Such temperature regulation means may comprise electrical connections for each deformation member 4 to connect it to an electrical power supply to supply electrical energy to the deformation members 4 consecutively from the deformation member 4 nearest to the second end 2.2 of the bag 2 to the deformation member 4 nearest to the first end 2.1 of the bag 2. In this manner the bag 2 can be emptied consecutively from the second end 2.2 to the first end 2.1 of the bag 2. FIG. 3 shows an intermediate step of such a consecutive emptying of the bag 2 where a rearward portion of the bag 2 at its second end 2.2 has already been emptied by shrinking the corresponding deformation members 4, while the remaining part of the bag 2 is still filled with liquid medicament.

The medicament container 1 may preferably be used for delivering one of an analgesic, an anticoagulant, insulin, insulin derivate, heparin, Lovenox, a vaccine, a growth hormone, a peptide hormone, a protein, antibodies and complex carbohydrates.

The invention claimed is:

1. A medicament container for a liquid medicament, the medicament container comprising:
   a deformable bag with an outlet and a plurality of deformation members consisting of a shape memory alloy and arranged to deform the deformable bag when the shape memory alloy passes from a first phase into a second phase by a phase transition, thereby changing the shape of the deformation member and squeezing a dose of the medicament through the outlet out of the bag, wherein the plurality of deformation members are arranged consecutively along the deformable bag; and
   temperature regulation means for changing the temperature of a deformation member to cause the phase transition of its shape memory alloy, wherein the temperature regulation means comprise electrical connections for each deformation member for connecting the plurality of deformation members to an electrical power supply.

2. The medicament container according to claim 1, characterized in that the shape memory alloy is a magnetic shape memory alloy.

3. The medicament container according to claim 1, characterized in that the plurality of deformation members stretch out over at least part of a longitudinal extension of the bag.

4. The medicament container according to claim 1, characterized in that the plurality of deformation members are located at an outer surface of the bag.

5. The medicament container according to claim 3, characterized in that each of the plurality of deformation members stretches out straightly in the first phase of its shape memory alloy and is rolled up spirally in the second phase of its shape memory alloy.

6. The medicament container according to claim 5, characterized by a core around which each of the plurality of deformation members is rolled up spirally in the second phase of its shape memory alloy.

7. The medicament container according to claim 3, characterized in that each of the plurality of deformation members stretches out as a helix around the bag, the radius of the helix being smaller in the second phase than in the first phase of the shape memory alloy.

8. The medicament container according to claim 7, characterized by a core stretching out over the axis of the helix.

9. An injection arrangement for delivering a liquid medicament comprising a medicament container according to claim 1.

10. An injection arrangement according to claim 9, characterized in that a valve and a hollow needle for piercing a patients skin are arranged at the outlet.

* * * * *